United States Patent [19]

Ingenbleek et al.

[11] Patent Number: 4,526,793

[45] Date of Patent: Jul. 2, 1985

[54] LIPID COMPOSITION FOR ORAL, ENTERAL OR PARENTERAL NUTRITION

[75] Inventors: Yves Ingenbleek, Corseaux; Helmut Traitler, Vevey, both of Switzerland; Jean-Yves Wessely, Bois-Colombes, France

[73] Assignee: Nestec, S.A., Vevey, Switzerland

[21] Appl. No.: 482,430

[22] Filed: Apr. 6, 1983

[30] Foreign Application Priority Data

Apr. 16, 1982 [CH] Switzerland .......................... 2314/82

[51] Int. Cl.³ .......................... A23D 5/00; A23L 1/30
[52] U.S. Cl. ........................................ 426/72; 426/74; 426/602; 426/607; 426/612
[58] Field of Search ............... 426/606, 607, 611, 612, 426/801, 72, 74, 602

[56] References Cited

U.S. PATENT DOCUMENTS

| | | | |
|---|---|---|---|
| 2,611,706 | 9/1952 | Bernhart et al. | 426/801 X |
| 3,542,560 | 11/1970 | Tomarelli et al. | 426/801 |
| 3,649,295 | 3/1972 | Bernhart | 426/801 X |
| 4,216,236 | 8/1980 | Müeller et al. | 426/801 X |

OTHER PUBLICATIONS

Horrobin, D., "Evening Primrose Oil", The Health Quarterly, vol. 6, No. 5, Sep./Oct. 1981, New Canaan, Ct., pp. 18, 19, 70 and 71.

*Primary Examiner*—Robert Yoncoskie
*Attorney, Agent, or Firm*—Vogt & O'Donnell

[57] ABSTRACT

There is disclosed a nutritional lipid composition that comprises an oil containing γ-linolenic acid, medium chain triglycerides and an edible oil containing $C_{12}$–$C_{18}$ lipid fractions. The oil containing γ-linolenic acid may be obtained from the pips or seeds of fruits of the genus Ribes.

10 Claims, No Drawings

LIPID COMPOSITION FOR ORAL, ENTERAL OR PARENTERAL NUTRITION

This invention relates to a lipid composition for oral, enteral or parenteral nutrition.

Numerous pathological situations in man require a considerable supply of lipids to remedy anomalies in the lipid metabolism or to make up for a specific deficiency (for example various digestive and nutritional disorders, specific needs in resuscitation, in intensive care and shock).

French Patent Application No. 2,490,631 for example mentions lipid compositions which are to be used in this type of situation and which comprise an oil containing $\gamma$-linolenic acid ($C_{18}:3\omega6$) in admixture with glycerol esters of $C_6$–$C_{12}$ fatty acids. The oil containing $\gamma$-linolenic acid which has been proposed is obtained from seeds of Oenothera biennis and Oenothera Lamarckiana (evening primrose). Glycerol esters of $C_6$–$C_{12}$ fatty acids make up at least 50% by weight of the lipid composition.

However, a composition of this type does not meet in optimum manner the requirements which have been mentioned above, because it contains an excess of $C_6$–$C_{12}$ triglycerides which are known as being strongly ketogenic, and because it does not contain any $C_{12}$–$C_{18}$ lipid fractions which nevertheless are essential to nutritional equilibrium during prolonged feeding of seriously ill patients.

The present invention provides a lipid composition which does not have the disadvantages of known compositions, and which provides lipids supplying:
caloric energy providing substrates for the balanced functioning of the internal metabolism,
essential fatty acids, the function of which is to participate in the regulation of numerous cellular structures and metabolisms, including the composition of the membranes and the synthesis of numerous active substances (prostaglandins, leucotrienes and thromboxanes).

The nutritional lipid composition according to the present invention is characterised in that it comprises:
(a) from 10 to 30% by weight of an oil containing $\gamma$-linolenic acid in the form of triglycerides,
(b) from 20 to 40% by weight of triglycerides of $C_6$–$C_{12}$ fatty acids, and
(c) from 50 to 70% by weight of an edible oil containing fatty acids in the form of triglycerides, at least 80% of the number of the fatty acids present being $C_{12}$ to $C_{18}$ fatty acids, the total of components (a) and (b) not exceeding 50% by weight of the composition.

$\gamma$-linolenic acid is a poly-unsaturated fatty acid which is metabolised by the organism into prostaglandins via dihomo-$\gamma$-linolenic acid and arachidonic (5, 8, 11, 14-eicosatetraenoic) acid, which is itself a constituent of cellular membranes, whereas $\alpha$-linolenic acid does not take part in this metabolic process in the same manner. The conversion of linoleic acid (C $18:2\omega6$) into $\gamma$-linolenic acid in the tissue is incomplete (4–20% compared to 90–98% for the conversion of $\gamma$-linolenic acid into arachidonic acid) and may not even occur when the enzyme $\Delta$-6-desaturase is absent or inactivated. $\gamma$-linolenic acid thus becomes essential in pathological situations (for example stress, major surgical and medical disorders, cancer, premature birth, senescence, etc.) in which this enzyme has proved to be deficient. Consequently lack of essential fatty acids results in a nutritional deficiency affecting all the metabolic processes which have been mentioned above and which may result in biochemical disorders or in organic lesions (for example coagulation disorders, skin lesions, endocrinal complaints, myocardiac lesions and hepatic, articular, neurological and mental disorders). The advantages afforded by a supply of $\gamma$-linolenic acid for the prevention or for the treatment of these anomalies are therefore evident.

According to the invention, the oil containing $\gamma$-linolenic acid is preferably an oil present in the pips of fruit of the genus Ribes, and contains at least 4% by weight of this acid in the form of triglycerides. This oil may be recovered by solvent extraction of pips or cake obtained as residues from juice pressing in the production of preserves and jellies, or from fermentation residues from the production of brandy, liqueurs and schnapps. These residues are available in large quantities and have usually been used up until now as fuel. Their lipid content ranges from 12 to 30% by weight depending on the starting material, and the lipid phase in turn contains from 4 to 19% by weight of $\gamma$-linolenic acid. Preferred fruits of the genus Ribes are blackcurrants (Ribes nigrum), redcurrants (Ribes rubrum) and gooseberries (Ribes ovacrispa or grossularia). By way of example, a process for extracting $\gamma$-linolenic acid is described in our copending application entitled "Nutritive compositions containing fatty substances and a process for the preparation thereof".

The fatty acid compositions of oils obtained from these fruits are, by weight, as follows:

| Fatty acids | Blackcurrant | Red currant | Gooseberry |
| --- | --- | --- | --- |
| C16:0 | 6–7% | 4–5% | 7–8% |
| C18:0 | 1–2% | 1–2% | 1–2% |
| C18:1 cis | 9–10% | 14–15% | 15–16% |
| C18:1 trans | 0.5% | 0.5–1% | 1–2% |
| C18:2$\omega$6 | 47–49% | 41–42% | 39–41% |
| C18:3$\omega$6 | 15–19% | 4–5% | 10–12% |
| C18:3$\omega$3 | 12–14% | 29–31% | 19–20% |
| C18:4$\omega$3 | 3–4% | 2.5–3.5% | 4–5% |

Blackcurrant oil is preferred because of its high content of $\gamma$-linolenic acid; it also contains from 1 to 2% by weight of unsaponifiable substances, such as aliphatic alcohols, hydrocarbons, tocopherols, squalene, $\beta$-sitosterol, campesterol and $\Delta$-7 stigmasterol.

Triglycerides of $C_6$–$C_{12}$ fatty acids, in particular $C_8$–$C_{10}$ fatty acids, commonly termed "medium chain triglycerides" represent an immediate source of energy. They may be obtained from coconut fat or palm kernel fat by hydrolysis, fractionation of the fatty acids (essentially $C_8$–$C_{10}$) by distillation and re-esterification with glycerol. They may also be extracted from Cuphea species, which contain 80–90% of $C_{10}$ fatty acid.

Fatty acids ingested in foods (after passage through the digestive tract), or injected intravenously, are utilised at catabolic sites or might be stored. They undergo oxidation in the mitochondrion ($\beta$-oxidation) terminating in the formation of acetyl radicals which enter into the Krebs cycle or, if there is a lack of oxaloacetic acid, they are converted into ketonic substances (hydroxybutyric acid and acetoacetic acid) in the liver. They thus provide a considerable amount of energy for maintaining the main synthesis functions of the organism.

However, in some pathological conditions ingested lipids are not absorbed, or are insufficiently absorbed by the digestive tract (hepatic insufficiency, biliary secretion insufficiency, pancreatic insufficiency, functional or organic insufficiency of the small intestine), and it is therefore indicated to supply medium chain triglycerides which are absorbed by the intestine much more easily than long chain fatty acids.

In addition, medium chain triglycerides penetrate directly into the mitochondrion (oxidation site) and unlike long chain fatty acids do not need a specific vector system. Finally, recent work has demonstrated a protecting effect of medium chain triglycerides on poly-unsaturated fatty acids by being oxidized preferentially, so that the poly-unsaturated fatty acids remain intact for their synthesis and structure functions. (S. C. Frost and M. A. Wells, Archives of Biochemistry and Biophysics, 1981, 211, 2, 537–546; D. Sailer and M. Muller, J.P.E.N., 1981, 5, 2, 115–119).

The edible oils present in the composition of the present invention may be of vegetable or animal origin and it should provide, inter alia, palmitic, stearic, oleic, linoleic and α-linolenic acids. Examples of suitable oils are corn, safflower, wheat germ, sunflower, peanut and cottonseed oils, with soya and grape seed oil being particularly preferred, especially for parenteral compositions as they contain appreciable quantities of unsaturated fatty acids (oleic, linoleic and α-linolenic). Butter oil and its fractions are also suitable.

Soya oil contains the following fatty acids:

| Fatty acids | % by weight |
| --- | --- |
| $C16:0$ | 9.9–12.1 |
| $C16:1\omega7$ | 0.2–0.4 |
| $C18:0$ | 1.3–4.8 |
| $C18:1\omega9$ | 22.5–31.2 |
| $C18:2\omega6$ | 48.9–54.7 |
| $C18:3\omega3$ | 5.2–8.5 |

Grape pip oil contains the following fatty acids:

| Fatty acids | % by weight |
| --- | --- |
| $C16:0$ | 6.7 |
| $C18:0$ | 3.9 |
| $C18:1$ cis | 14.2 |
| $C18:1$ trans | 0.7 |
| $C18:2\omega6$ | 74.2 |
| $C18:3\omega3$ | 0.3 |

α-linolenic acid ($C18:3\omega3$) cannot be synthesized by mammals, but it does not appear to reduce lesions induced in animals by a deficiency of essential fatty acids. However, a recent publication (R. T. Holman, S. B. Johnson, T. F. Hatch, The Amer. Journal of Clinical Nutrition, 1982, 35, 617–623), describes the case of a young child receiving a lipid perfusion without α-linolenic acid who developed symptoms of deficiency of this fatty acid (torpor, paraesthesiae, backwardness in learning to walk, pains in the lower limbs) which became completely degressive when α-linolenic acid was added to the parenteral diet.

It should also be noted that α-linolenic acid is a precursor of type 3 prostaglandins derived from eicosapentaenoic acid ($C20:5\omega3$) in the synthesis of which it is the starting material.

It is generally accepted that these $C_{12}$–$C_{18}$ fractions are transported by a specific vector, carnitine, the endogenous synthesis of which takes place from lysine and methionine found in a normal diet. In the pathological conditions described above, however, it is possible that synthesis of carnitine is depressed. It is therefore desirable to provide an exogenous supply of carnitine, enterally or parenterally, and hence carnitine may advantageously be added to the lipid composition.

The compositions also contain liposoluble vitamins either naturally present in the oils or added in physiological quantities as required to meet specific needs.

The minimum requirements of a healthy adult
of linoleic acid are about 3% of the daily caloric intake
of α-linolenic acid are about 0.5% of the daily caloric intake
of γ-linolenic acid are about 2 g/24 hours.

Bearing in mind these different considerations relating to the adsorption of essential fatty acids and medium chain triglycerides, the lipid composition of the present invention preferably has the following composition:

(a) from 10 to 20% by weight of an oil containing γ-linolenic acid in the form of triglycerides, (b) from 20 to 30% by weight of medium chain triglycerides, and (c) from 60 to 70% by weight of a vegetable oil containing fatty acids in the form of triglycerides, at least 80% of the number of the fatty acids present being $C_{12}$ to $C_{18}$ fatty acids, the total of (a) and (b) not exceeding 40% of the composition.

These compositions are especially suitable for use in parenteral nutrition.

The compositions of the invention are presented in forms adapted to their method of administration. Thus, for oral administration they may be in dosage units formulated for example as (gelatine) capsules containing the lipid composition in suitable amounts, or as emulsions with an aqueous phase nutrients such as proteins or amino acids, carbohydrates trace elements minerals and/or vitamins, and if desired antioxidants and emulsifiers. Such emulsions may for convenience be dried and reconstituted with water for consumption. Emulsions of this type may also be administered enterally.

Compositions for parenteral administration will generally be in emulsion form, and the aqueous phase may also contain nutrients as mentioned above. Specific examples of nutrients that may be incorporated in the emulsions (enteral and parenteral) are glucose, polyols (glycerol, xylitol, sorbitol) and carnitine. Among suitable emulsion stabilisers (emulsifiers) may be mentioned egg and soya phosphatides and their fractions; tocopherols are the preferred antioxidants.

Finally, the emulsions may be iso- or hypertonic; for parenteral administration they are sterile and pyrogen free.

The following Examples, in which all parts and percentages are expressed by weight unless otherwise stated, are given only for the purpose of illustrating the invention. The abbreviation GLA is used to designate γ-linolenic acid.

EXAMPLE 1

An isotonic aqueous emulsion for parenteral nutrition is prepared by first mixing:

| | |
| --- | --- |
| Blackcurrant pip oil, containing 2% GLA | 12% |
| Medium chain triglycerides | 20% |
| Soya oil | 68% |

6% of emulsifier (soya phosphatides, on weight of lipids) are added and the mixture is sterilised.

Sterile water is added in an amount sufficient to provide 100 g of lipids per liter of finished emulsion. Emulsification is then effected by homogenisation at 140–180 bars under sterile conditions, at 55° C. (below the phase inversion temperature of the emulsion) until the lipids are reduced to a particle size below 0.5 μm.

The emulsion is filled aseptically into 1 liter containers and as it is now very stable, the containers are sterilised at 110°–130° C. for 20–30 minutes.

Alternatively, the emulsification may be effected in a colloid mill.

EXAMPLE 2

A hypertonic emulsion for parenteral nutrition containing 25 g/liter of glucose, is prepared by following the procedure described in Example 1 (same ingredients and amounts) except that the glucose is dissolved in the water before emulsification.

Further parenteral emulsions are prepared with xylitol, sorbitol and glycerol instead of glucose, in amounts giving a final concentration of 25, 50 and 100 g/liter.

EXAMPLE 3

An aqueous hypertonic emulsion for parenteral nutrition is prepared by the procedure described in Example 1 but using the following ingredients:

| Blackcurrant pip oil, containing 2 g of GLA | 12 g |
|---|---|
| Medium chain triglycerides | 20 g |
| Grape seed oil | 60 g |
| Egg phosphatides (as emulsifier) | 8 g |
| Carnitine } in aqueous phase | 2 g |
| Glucose | 50 g |
| Sterile water q.s.p. | 1 liter |

EXAMPLE 4

Following the procedure described in Example 1 a hypertonic emulsion for parenteral nutrition is prepared from the following ingredients:

| Blackcurrant seed oil, providing 4 g of GLA | 24 g |
|---|---|
| Medium chain triglycerides | 40 g |
| Grape seed oil | 120 g |
| Egg phosphatides (emulsifier) | 16 g |
| Glucose (dissolved in water) | 50 g |
| Sterile water q.s.p. | 1 liter |

EXAMPLE 5

A formula for feeding premature infants is prepared by the procedure described in U.S. Pat. No. 4,216,236 using, per 100 g of finished product, the following ingredients:

| Blackcurrant seed oil, containing 0.4 g of GLA | 2.4 g |
|---|---|
| Medium chain triglycerides | 9.6 g |
| Butter fat | 12.0 g |
| Lactose | 41.6 g |
| Glucose | 56.9 g |
| Casein | 4.4 g |
| Whey proteins | 14.4 g |

These ingredients contribute, per 100 g:

| Calcium | 350 mg |
|---|---|
| Phosphorus | 200 mg |
| Potassium | 370 mg |

| -continued | |
|---|---|
| Sodium | 103 mg |

Mineral salts and vitamins are added in amounts such that 100 g of product also contain a minimum of:

| Iron | 6.0 mg |
|---|---|
| Copper | 0.3 mg |
| Zinc | 1.8 mg |
| Iodine | 25 μg |
| Folic acid | 80 μg |
| Vitamin C | 200 mg |
| Vitamin E | 10 mg |
| Vitamin $B_1$ | 0.35 mg |

For consumption 15 g of powder are dispersed in 90 ml of water.

EXAMPLE 6

A composition for enteral nutrition of the aged is prepared from the following ingredients:

| Blackcurrant seed oil, containing 2.4 kg GLA | 36 kg |
|---|---|
| Medium chain triglycerides | 24 kg |
| Soya oil | 60 kg |
| Whey lactalbumin, pancreatically hydrolysed, containing 20% free amino acids and 18% peptides of molecular weight below 1000 | 117.5 kg |
| Maltodextrins | 270 kg |
| Sucrose | 94.5 kg |
| Pregelatinised starch | 10 kg |
| Minerals and vitamins | As required |

The starch is dissolved in 333 kg cold water. Separately, the lactalbumin is dissolved in 500 kg of water at 65° C. and the minerals are added followed by the starch solution, maltodextrins, sucrose and, in a 10% aqueous solution, the vitamins. The lipid ingredients, pre-heated to 65° C., are then added and the phased stirred together. The mixture is passed at 65° C. through a colloid mill and then through a homogeniser at 300 bars. The homogenized blend is pasteurised at 105° C. for 1 minute, cooled to 65° C. and again homogenized, at 400 bars. The blend is finally spray-dried and packed under nitrogen in airtight containers.

For use 15 g powder are dispersed in 90 ml of water.

We claim:
1. A nutritional lipid composition comprising:
   (a) from 10 to 30% by weight of an oil containing γ-linolenic acid in the form of triglycerides, said oil being obtained from the pips or seeds of fruits of the genus Ribes,
   (b) from 20 to 40% by weight of triglycerides of $C_6$–$C_{12}$ fatty acids, and
   (c) from 50 to 70% by weight of an edible oil containing fatty acids in the form of triglycerides, at least 80% of the number of the fatty acids present being $C_{12}$ to $C_{18}$ fatty acids, the total of components (a) and (b) not exceeding 50% by weight of the composition.
2. A composition according to claim 1, comprising:
   (a) from 10 to 20% by weight of oil containing γ-linolenic acid in the form of triglycerides,
   (b) from 20 to 30% by weight of medium chain triglycerides, and
   (c) from 60 to 70% by weight of a vegetable oil containing $C_{12}$–$C_{18}$ fatty acids in the form of triglycer- ides, the total of components (a) and (b) not exceeding 40% by weight of the composition.

3. A composition according to claim 1 in which the fruit is *Ribes nigrum*.

4. A composition according to claim 1 in which the oil containing $C_{12}$ to $C_{18}$ fatty acid triglycerides is grape seed oil or soya oil.

5. An emulsion adapted for oral, enteral, or parenteral administration comprising a composition according to claim 1 emulsified with an aqueous phase.

6. An emulsion according to claim 5 comprising an emulsifier.

7. A composition according to claim 6 in which the emulsifier is an egg or soya phosphatide or a fraction thereof.

8. An emulsion according to claim 5, 6 or 7 in which the aqueous phase contains at least one member selected from the group consisting of a carbohydrate, a polyol, a protein, an amino acid, a vitamin, a mineral salt and carnitine.

9. An emulsion according to claim 5 in dried form.

10. A composition according to claim 2 in which said vegetable oil contains at least one member selected from the group consisting of oleic acid, linoleic acid and γ-linolenic acid.

* * * * *

UNITED STATES PATENT AND TRADEMARK OFFICE
CERTIFICATE OF CORRECTION

PATENT NO. : 4,526,793
DATED : July 2, 1985
INVENTOR(S) : Yves Ingenbleek, et al.

It is certified that error appears in the above—identified patent and that said Letters Patent is hereby corrected as shown below:

Column 8, Claim 10, line 13, "$\gamma$-linolenic acid" should read -- $\alpha$-linolenic acid --.

Signed and Sealed this

Fifteenth Day of October 1985

[SEAL]

Attest:

Attesting Officer

DONALD J. QUIGG

*Commissioner of Patents and Trademarks—Designate*